(12) United States Patent
Nishida et al.

(10) Patent No.: US 7,547,414 B2
(45) Date of Patent: Jun. 16, 2009

(54) AUTOMATIC ANALYZER

(75) Inventors: Masaharu Nishida, Hitachinaka (JP); Hiroshi Ohga, Ohmiya (JP)

(73) Assignees: Hitachi High-Technologies Corporation, Tokyo (JP); Hitachi Science Systems, Ltd., Ibaraki (JP)

( * ) Notice: Subject to any disclaimer, the term of this patent is extended or adjusted under 35 U.S.C. 154(b) by 613 days.

(21) Appl. No.: 10/898,243

(22) Filed: Jul. 26, 2004

(65) Prior Publication Data

US 2005/0047964 A1    Mar. 3, 2005

(30) Foreign Application Priority Data

Jul. 25, 2003    (JP)    ............... 2003-201460

(51) Int. Cl.
*G01N 21/00*    (2006.01)

(52) U.S. Cl. ............... 422/67; 422/63; 422/64; 422/65; 422/99; 422/100; 436/47; 436/50; 220/4.01

(58) Field of Classification Search ............ 422/63–65, 422/99–101, 67; 436/180, 47, 50; 220/4.01
See application file for complete search history.

(56) References Cited

U.S. PATENT DOCUMENTS 5,051,238 A    9/1991  Umetsu et al.
5,424,036 A *  6/1995  Ushikubo ............... 422/64
5,700,429 A * 12/1997  Buhler et al. ........... 422/104
5,776,784 A    7/1998  Kegelman et al.
5,827,479 A   10/1998  Yamazaki et al.

FOREIGN PATENT DOCUMENTS

| DE | 43 13 807 | 11/1993 |
| JP | 8-271517 | 10/1996 |
| WO | WO93/02348 | 2/1993 |

* cited by examiner

*Primary Examiner*—Jill Warden
*Assistant Examiner*—Jyoti Nagpaul
(74) *Attorney, Agent, or Firm*—Mattingly & Malur, PC

(57) ABSTRACT

For installing reagent bottles in a reagent disk, the operator needs to install them while confirming the orientation of each reagent bottle. However, the operator will groan under a psychological burden in working while confirming the orientation. If the operator installs a reagent cassette in wrong orientation, the result of measurement will be erroneous, possibly leading to a grave testing error particularly in a blood analyzer. An automatic analyzer comprises a recording medium for recording information on placement of a plurality of types of reagents contained in a single reagent container, a reagent container disk capable of carrying a plurality of the reagent containers, an information reader for reading information recorded on the recording medium, and a reagent dispense controller for controlling which of reagents is dispensed by a reagent dispenser based on the information read by medium information reader.

5 Claims, 5 Drawing Sheets

FIG.3A
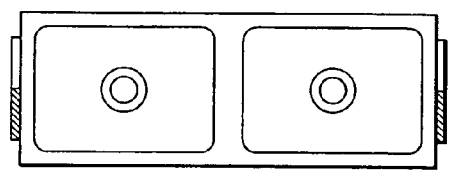
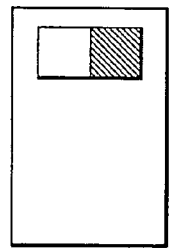
FIG.3B
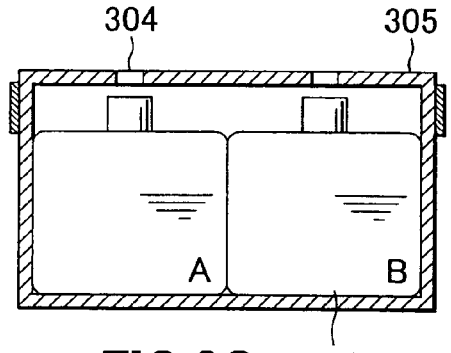
FIG.3C
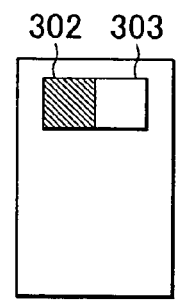
FIG.3D

WHEN REAGENT CASSETTE IS INSTALLED IN NORMAL ORIENTATION

OUTPUT WAVEFORM OF OPTICAL SENSOR

WHEN REAGENT CASSETTE IS INSTALLED IN OPPOSITE ORIENTATION

OUTPUT WAVEFORM OF OPTICAL SENSOR

WHEN NO REAGENT CASSETTE IS PLACED

OUTPUT WAVEFORM OF OPTICAL SENSOR

AUTOMATIC ANALYZER

BACKGROUND OF THE INVENTION

The present invention relates to an automatic analyzer for performing qualitative/quantitative analyses on biogenic components such as blood, urine, and the like, and more particularly, to an automatic analyzer which employs the same reagent container for containing a plurality of reagents.

A turn-table type reagent disk having a circular table for rotating reagent bottles and reagent cassettes installed along the circumference thereof is prevalent in automatic analyses because this type of reagent disk can perform a random access analysis with minimal movements of a nozzle for aspirating a reagent.

An analyzer generally stores information on previously registered reagents, analysis items measured using the reagents, and numbers associated with positions on a reagent disk at which reagents are placed. For making a measurement, a required reagent is rotated to a reagent aspirating position, and a nozzle for aspirating the reagent is moved to position above a reagent cassette to aspirate the reagent.

A conventional automatic analyzer as described above is disclosed, for example, in JP-A-8-271517.

SUMMARY OF THE INVENTION

A currently dominant way is to contain one type of reagent in one reagent container. However, since there are multiple analysis items which are measured with a plurality of reagents added in course of a chemical reaction, for example, multiple items which are measured using a plurality of reagents, a reagent cassette is now used in such a manner that a plurality of reagents are contained in a single container. A reagent cassette which permits a plurality of reagents to be contained in a single container tends to have a symmetric shape in order to make the volume as small as possible. When the operator installs such a reagent bottle on a reagent disk, the operator must confirm the orientation of the reagent bottle before installation. However, the operator will groan under a psychological burden in working while confirming the orientation. If the operator installs a reagent cassette in a wrong orientation, the result of measurement will be erroneous, possibly leading to a grave testing error particularly in a blood analyzer.

While it is contemplated to mechanically install a reagent container after the orientation is automatically confirmed, such a strategy will entail an increase in the size and cost of the analyzer.

It is an object of the present invention to provide a compact and low-cost automatic analyzer which prevents erroneous results of measurements due to a mistake in installing a reagent container in terms of orientation.

To achieve the above object, the present invention provides an automatic analyzer which includes a reagent container for containing a plurality of types of reagents in the same housing, reagent container holding means capable of carrying a plurality of the reagent containers, and reagent dispensing means for dispensing a reagent contained in the reagent container on the reagent container holding means. The reagent container has a recording medium adhered thereon for recording information on placement of a plurality of types of reagents contained therein. The automatic analyzer further includes information reading means for reading information recorded on the recording medium, and reagent dispense control means for controlling which of reagents is dispensed by the reagent dispensing means based on the information read by the information reading means.

The information recording medium may be an IC or the like which has a function of reading and writing a bar code or information. Instead of the bar code, the information recording medium may be made of a combination of a plurality of plates in different colors. The information reading means may be any of those which optically read information, utilize the magnetism, utilize electromagnetic waves, and the like in accordance with the particular recording medium. A nozzle for aspirating a reagent is preferably controlled based on the arrangement of reagents within the reagent container (reagent cassette) when the reagent cassette is installed in normal orientation and the arrangement of reagents when the reagent cassette is installed in opposite orientation.

The foregoing function allows the operator to install reagent cassettes in the reagent container holding means without awareness of the orientation in which each reagent cassette is installed.

BRIEF DESCRIPTION OF THE DRAWINGS

FIGS. 3A to 3D illustrate a reagent cassette in a front view, a top plan view and side views;

DETAILED DESCRIPTION OF THE PREFERRED EMBODIMENTS

Figure 1:
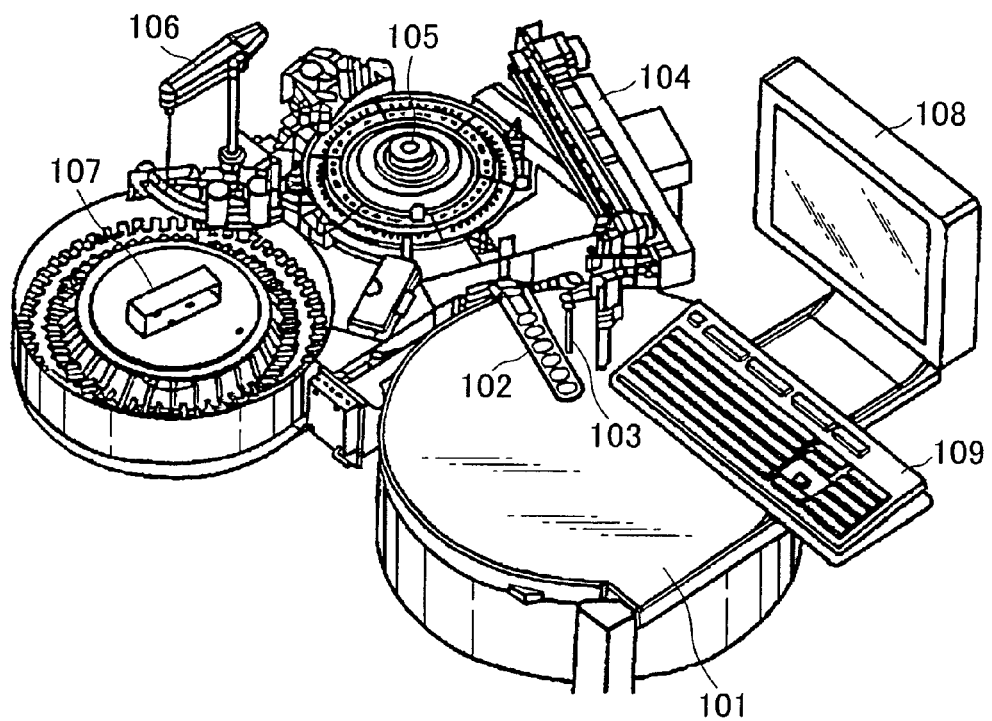
FIG. 1 is a perspective view generally illustrating an automatic analyzer according to one embodiment of the present invention.
Figure 2:
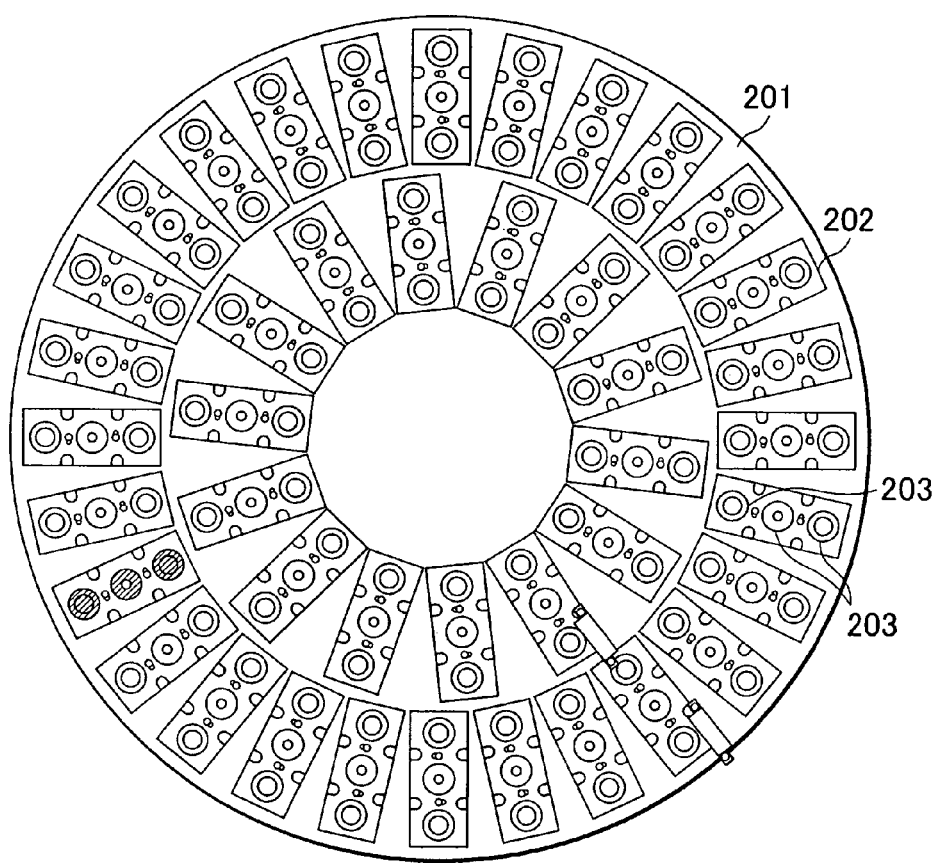
FIG. 2 is a top plan view of reagent cassettes when they are installed in a reagent disk.

FIG. 1 generally illustrates an automatic analyzer according to one embodiment of the present invention. FIG. 2 illustrates in a top plan view how reagent cassettes (reagent containers) are installed in a reagent disk.

In a reagent disk 101, a number of reagent cassettes 202 are installed along the inner and outer peripheries of the reagent disk 101, as illustrated in FIG. 2. Each of the reagent cassettes 202 is manually installed by the operator from an opening, not shown, of the reagent disk 101 for introducing the reagent cassette. The reagent disk 101 has six openings 102 for dispensing reagents which are positioned corresponding to openings 203 of the reagent cassettes 202 installed along the outer and inner peripheries of the reagent disk 101. A reaction disk 105 reacts a sample placed on a sample disk 107, aspirated by a sample nozzle 106 and delivered into a reaction container, with a reagent to analyze the sample.

A monitor 108 and a keyboard 109, which function as a display and an input device, respectively, are connected to a personal computer, not shown. A reagent cassette which contains a reagent required for a measurement is placed below the openings 102 by rotating the reagent disk 101, and the reagent nozzle 103 is moved to the position of the appropriate reagent for aspiration.

Next, description will be made on how to detect the orientation of an installed reagent cassette in accordance with one embodiment.

FIG. 3A includes a top plan view of a reagent cassette 305. There is a plurality of reagent bottles 301 in the reagent cassette 305 as shown in FIG. 3C. While the following description is made in connection with a reagent cassette which accommodates two reagent bottles, the number of reagent bottles in a reagent cassette is not limited to two. Reagents A, B composed of different components are contained in the respective reagent bottles 301. If the two reagents are erroneously used, a resulting measured value is an error. The reagent cassette 305 has openings 304 through which the associated reagents are aspirated. A black label 302 and a white label 303 are adhered on each side of the reagent cassette 305.

Figure 4A:
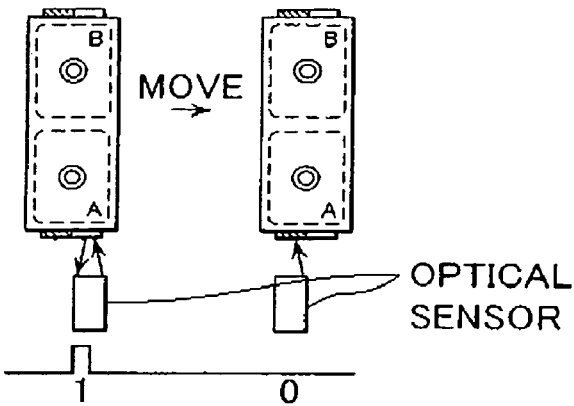
FIGS. 4A to 4C show the principle of detecting the orientation of an installed reagent cassette.
Figure 4B:
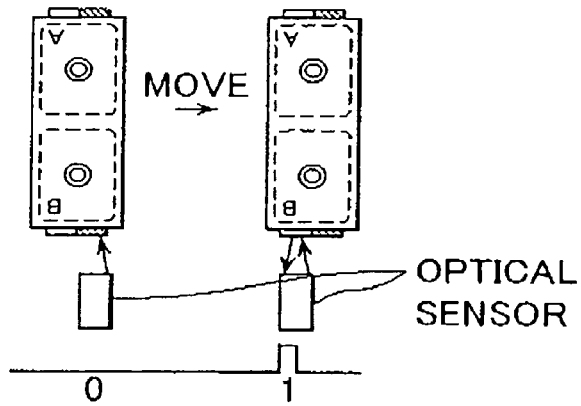
Figure 4C:
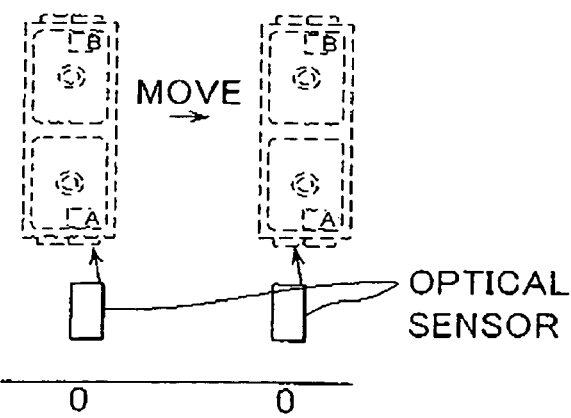

As can be seen in left and right lateral views of FIGS. 3B and 3D, the black labels 302 and white labels 303 are adhered in bilateral asymmetry. FIGS. 4A to 4C show the principle of detecting the orientation of an installed reagent cassette. The labels 302, 303 are read by optical sensors at a reading position 1 and a reading position 2, respectively. At the reading position 1, the white label 303 is read.

Each of the optical sensors generates an output waveform which is at high level when it detects the white label 303, and at low level when it detects the black label 302, where the H level corresponds to logical "1" and the L level corresponds to logical "0."

Each of the sensors, which is fixed at an appropriate position, reads the label adhered on a moving reagent cassette. The read timing may be detected by another sensor, or determined by measuring the distance by which the reagent cassette has moved, or by other methods not particularly defined by the present invention. When the reagent cassette is installed in normal orientation, the optical sensor reads the white label 303 at the reading position 1. In this event, the optical sensor generates an H level which corresponds to logical "1" in digital domain. Next, the reagent cassette is moved to the reading position 2 at which the optical sensor reads the black label 302, causing the optical sensor to generate an L level which corresponds to logical "0" in digital domain. In this event, a combination of the logical values detected by the two optical sensors presents a digital value "10." On the other hand, when the reagent cassette is installed in opposite orientation, one of the optical sensors reads the black label 302 at the reading position 1, while the other of the optical sensors reads the white label 303 at the reading position 2. Therefore, when the aforementioned logic is applied in this event, a combination of the detected logical values presents a digital value "01." By a comparison of this digital value with that generated when the reagent cassette is installed in normal orientation, or by previously defining that the digital value "01" indicates a reagent cassette installed in opposite direction, it is possible to determine that the reagent cassette is wrong in orientation. Next, when no reagent cassette is placed, both the optical sensors at the reading positions 1, 2 output the L level, resulting in a digital value "00." By a comparison of this digital value with the normal digital value, or by previously defining that the digital value "00" indicates the absence of the reagent cassette, it is possible to determine that there is no reagent cassette.

By sensing the orientation of the reagent cassette as described above, a central controller of the analyzer can recognize whether the reagent cassette 202 is place in normal or opposite orientation. Also, by previously registering the arrangement of reagents in the reagent cassettes 202 when the respective reagent cassettes 202 are installed in normal or opposite orientation, it is possible to recognize the positions of reagents within the reagent cassettes 202 placed in the reagent disk 201.

Figure 5A:
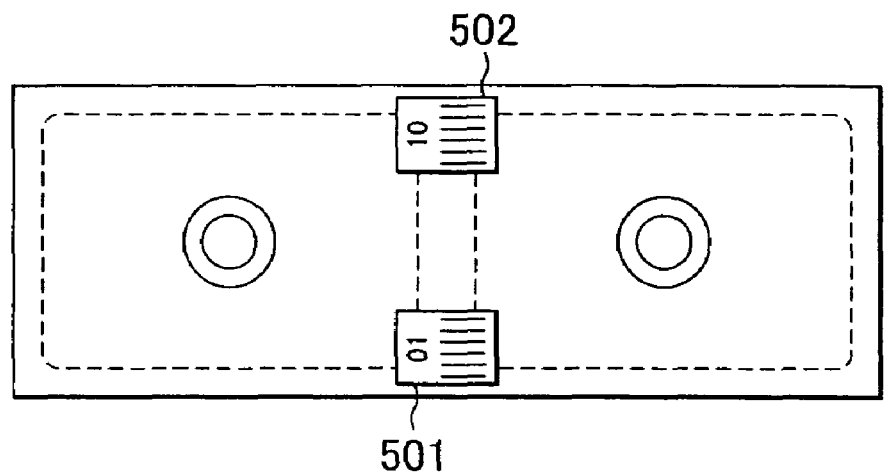
FIGS. 5A and 5B illustrate the reagent cassette according to a second embodiment in a top plan view and a front view.
Figure 5B:
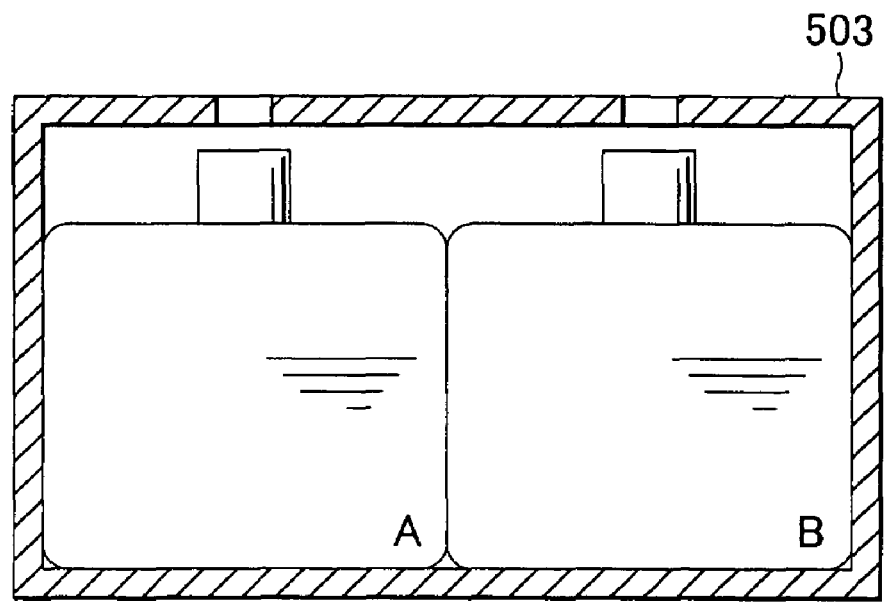

FIGS. 5A and 5B illustrate a reagent cassette 503 according to a second embodiment. Two types of bar codes are adhered on the top of the reagent cassette 503. A bar code reader reads, from above the reagent cassette 503, one of numbers represented by the bar codes first, and then reads the other number at the second time. By recognizing the numbers read by the bar code reader in order, it is possible to recognize the orientation in which the reagent cassette 503 is installed. The bar code is a mere exemplary means of recognizing numbers, and a wireless discriminator may be employed to recognize numbers to identify the orientation of the reagent cassette.

The automatic analyzer of the present invention can significantly reduce the psychological burden of the operator because of its ability to eliminate the installation of reagent cassettes in wrong orientation due to erroneous manipulations of the operator, which can give rise to errors in measured values. Since the automatic analyzer of the present invention can automatically confirm the orientation of reagent cassettes placed in a reagent disk in a short time, the operator is only required to work for a short time, and is therefore less burdened in terms of time.

What is claimed is:

1. An automatic analyzer comprising:
   reagent container holding means for holding a plurality of reagent containers;
   at least two labels attached to each of the reagent containers, said two labels indicating different information from each other;
   a discriminator for discriminating between said at least two labels attached to said reagent container;
   an orientation sensing means for sensing an orientation of said reagent container on said reagent container holding means on a basis of said information discriminated by said discriminator; and
   wherein said reagent container holding means comprises a reagent disk for arranging said reagent containers along a circumference of the reagent disk, said labels being attached on each of an outer peripheral surface and an inner peripheral surface of each of the reagent containers installed in said reagent disk.

2. An automatic analyzer according to claim 1, wherein:
   said orientation sensing means senses presence or absence of said reagent container on said reagent container holding means.

3. An automatic analyzer according to claim 1, wherein:
   said labels comprise a combination of two plates different in color from each other.

4. An automatic analyzer according to claim 1, wherein:
   said labels comprise a combination of two plates different in color from each other.

5. An automatic analyzer according to claim 1, wherein:
   said labels include barcode information.

* * * * *